(12) United States Patent
Beachy et al.

(10) Patent No.: US 8,067,608 B2
(45) Date of Patent: Nov. 29, 2011

(54) HEDGEHOG PATHWAY ANTAGONISTS

(75) Inventors: Philip A. Beachy, Towson, MD (US); James K. Chen, Mountain View, CA (US); Anssi J. Taipale, Helsinki (FI)

(73) Assignee: The Johns Hopkins University, Baltimore, MD (US)

( * ) Notice: Subject to any disclaimer, the term of this patent is extended or adjusted under 35 U.S.C. 154(b) by 162 days.

(21) Appl. No.: 10/573,945

(22) PCT Filed: Sep. 29, 2004

(86) PCT No.: PCT/US2004/032482
§ 371 (c)(1),
(2), (4) Date: Mar. 7, 2007

(87) PCT Pub. No.: WO2005/033288
PCT Pub. Date: Apr. 14, 2005

(65) Prior Publication Data
US 2007/0232661 A1    Oct. 4, 2007

Related U.S. Application Data

(60) Provisional application No. 60/507,164, filed on Sep. 29, 2003, now abandoned.

(51) Int. Cl.
*C07D 213/56* (2006.01)
*A61K 31/44* (2006.01)

(52) U.S. Cl. ........................................ 546/337; 514/357
(58) Field of Classification Search .................. 546/337; 514/357
See application file for complete search history.

(56) References Cited

FOREIGN PATENT DOCUMENTS
WO    WO 2004056774 A2 *    7/2004

OTHER PUBLICATIONS

Hcaplus 109:73373.*
Hcaplus 1999:48617.*
Patani, George, et. al., "Bioisosterism: A Rational Approach in Drug Design", Chem. Rev. 1996, 3147-3176.*
HCAPLUS 109:73373 1988.*
Patani, George, et. al., "Bioisosterism: A Rational Approach in Drug Design", Chem. Rev. , 3147-3176, 1996.*
Hcaplus 1999:48617, "Preparation of N-[(aminoalkoxy)phenyl]benezamides and analogs as CCR5 receptor ligands", Bondinell et. al., WO 9901127, Nov. 4, 1999.*

* cited by examiner

*Primary Examiner* — Janet Andres
*Assistant Examiner* — Heidi Reese
(74) *Attorney, Agent, or Firm* — DLA Piper LLP (US)

(57) ABSTRACT

Aromatic compounds for treating various diseases and pathologies are disclosed. The methods use of such compounds are also provided. Accordingly, the present invention makes available methods and compositions for inhibiting aberrant growth states resulting from hedgehog gain-of-function, ptc loss-of-function or smoothened gain-of-function.

6 Claims, No Drawings

HEDGEHOG PATHWAY ANTAGONISTS

CROSS REFERENCE TO RELATED APPLICATIONS

This application is a 35 USC §371 National Stage application of PCT Application No. PCT/US2004/032482 filed Sep. 29, 2004; which claims the benefit under 35 USC §119(e) to U.S. Application Ser. No. 60/507,164 filed Sep. 29, 2003, now abandoned. The disclosure of each of the prior applications is considered part of and is incorporated by reference in the disclosure of this application.

GRANT INFORMATION

This invention was made with government support under Grant Nos. CA095957-02 and HD39306-4 awarded by the National Institutes of Health. The United States government has certain rights in this invention.

BACKGROUND OF THE INVENTION

1. Field of the Invention

The present invention relates generally to the use of compounds to treat a variety of disorders, diseases and pathologic conditions and more specifically to the use of various aromatic compounds for inhibiting signaling pathways.

2. Background Information

Pattern formation is the activity by which embryonic cells form ordered spatial arrangements of differentiated tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families.

Members of the Hedgehog family of signaling molecules mediate many important short- and long-range patterning processes during invertebrate and vertebrate development. Exemplary hedgehog genes and proteins are described in PCT publications WO 95/18856 and WO 96/17924. The vertebrate family of hedgehog genes includes at least four members, three of which, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh is primarily involved in morphogenic and neuroinductive activities. Given the critical inductive roles of hedgehog polypeptides in the development and maintenance of vertebrate organs, the identification of hedgehog interacting proteins and their role in the regulation of gene families known to be involved in cell signaling and intercellular communication provides a possible mechanism of tumor suppression.

The ability to modulate one or more genes that are part of the hedgehog signaling cascade thus represents a possible therapeutic approach to several clinically significant cancers. A need therefore exists for methods and compounds that inhibit signal transduction activity by modulating activation of a hedgehog, patched, or smoothened-mediated signal transduction pathway, such as the Hedgehog signaling pathway, to reverse or control aberrant growth.

SUMMARY OF THE INVENTION

The present invention provides various methods and compounds for inhibiting activation of signaling pathways, such as the Hedgehog pathway e.g., to inhibit aberrant growth states resulting from phenotypes such as ptc loss-of-function, hedgehog gain-of-function, or smoothened gain-of-function.

The present invention makes available methods and reagents, comprising contacting the cell with an agent, such as an aromatic compound, in a sufficient amount to agonize a normal ptc activity, antagonize a normal hedgehog activity, or antagonize smoothened activity, e.g., to reverse or control the aberrant growth state.

According to one embodiment of the invention, compounds having the structure (I) are provided, or a pharmaceutically acceptable salt thereof:

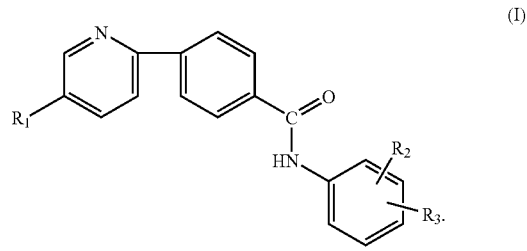

(I)

According to one embodiment of the invention, compounds having the structure (II) are provided, or a pharmaceutically acceptable salt thereof:

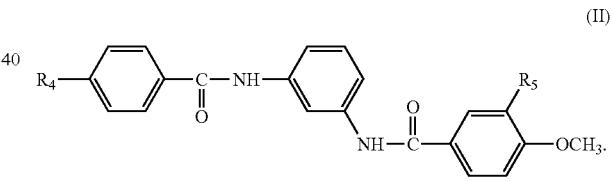

(II)

According to one embodiment of the invention, compounds having the structure (III) are provided, or a pharmaceutically acceptable salt thereof:

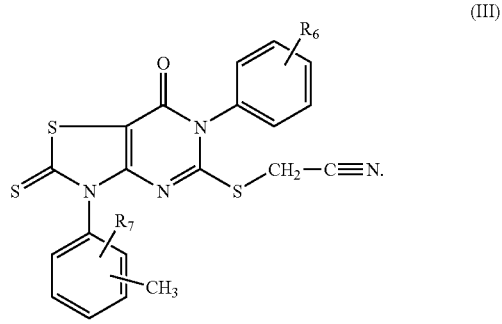

(III)

According to one embodiment of the invention, compounds having the structure (IV) are provided, or a pharmaceutically acceptable salt thereof:

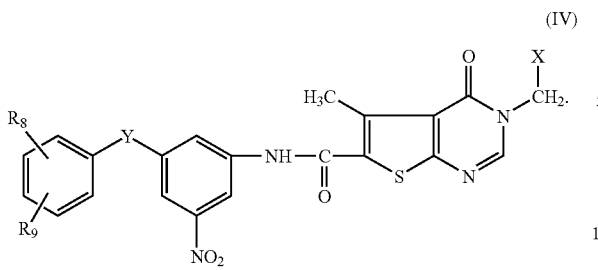

(IV)

According to one embodiment of the invention, compounds having the structure (V) are provided, or a pharmaceutically acceptable salt thereof:

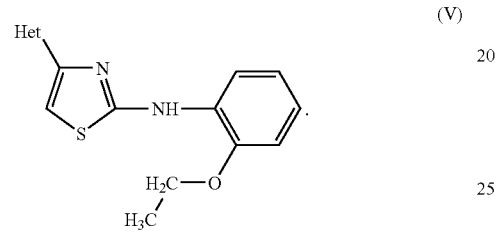

(V)

According to one embodiment of the invention, compounds having the structure (VI) are provided, or a pharmaceutically acceptable salt thereof:

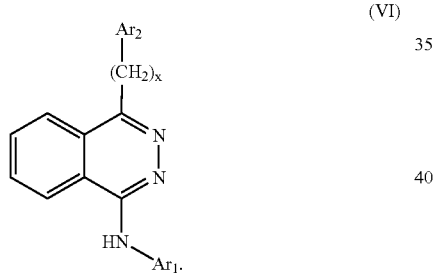

(VI)

According to one embodiment of the invention, compounds having the structure (VII) are provided, or a pharmaceutically acceptable salt thereof:

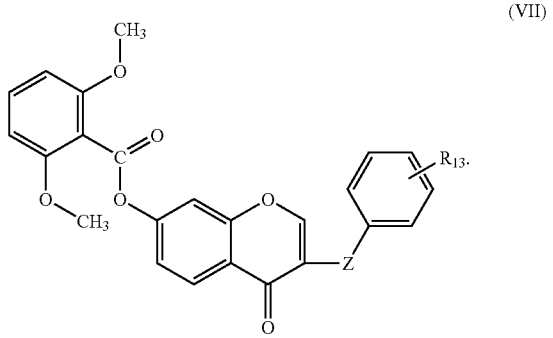

(VII)

According to one embodiment of the invention, compounds having the structure (VIII) are provided, or a pharmaceutically acceptable salt thereof:

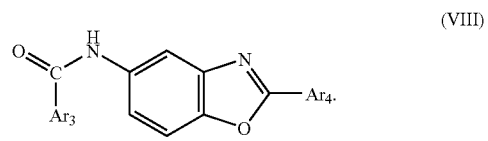

(VIII)

According to one embodiment of the invention, compounds having the structure (IX) are provided, or a pharmaceutically acceptable salt thereof:

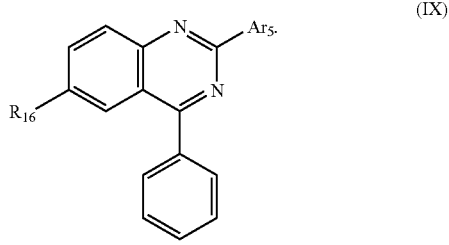

(IX)

According to one embodiment of the invention, compounds having the structure (X) are provided, or a pharmaceutically acceptable salt thereof:

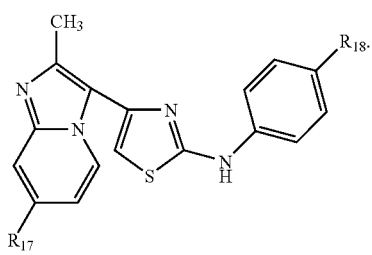

(X)

In compounds (I)-(X), the following substitutents can be used independently of any other substituents:

$R_1$ can be an alkyl, $R_2$ can be any of hydrogen, an alkyl, halogen, and an alkoxy group, $R_3$ can be any of an unsubstituted or substituted alkyl group, halogen, an alkoxy group, acetyl group, or nitro group, $R_4$ can be tert-butyl or chlorine, $R_5$ can be nitro group or bromine, $R_6$ can be methyl or ethoxy group, $R_7$ can be hydrogen or methyl, $R_8$ can hydrogen or methyl, $R_9$ can be any of hydrogen, chlorine or fluorine, $R_{10}$ can be methyl or chlorine, $R_{11}$ can be any of hydrogen, methyl, or chlorine, $R_{12}$ can be any of hydrogen,

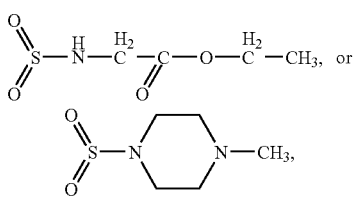

$R_{13}$ can be any of chlorine, bromine, or methoxy, $R_{14}$ can be hydrogen or bromine, $R_{15}$ can be tert-butyl or iodine, $R_{16}$ can be hydrogen or methyl, $R_{17}$ can be hydrogen or methyl, $R_{18}$ can be any of methyl, methoxy, or ethoxy, X can be ethyl or fluorophenyl, Y can be an atom of oxygen or sulfur, Z can be an atom of oxygen or a single α-bond, "Het" is a heterocyclic moiety that can be a pyridyl or thiazolyl, $Ar_1$ can be any of aromatic moieties:

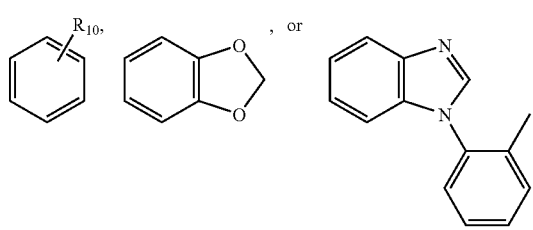

$Ar_2$ can be an aromatic moiety having the structure:

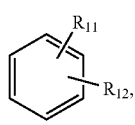

$Ar_3$ can be an aromatic moiety having the structure:

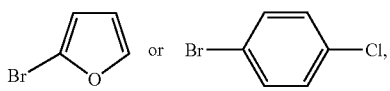

$Ar_4$ can be an aromatic moiety having the structure:

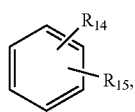

$Ar_5$ can be any of aromatic moieties:

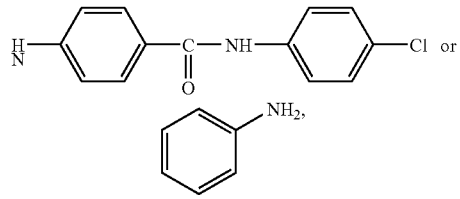

and
x is an integer that can have the value of 0 or 1.

According to one embodiment of the invention, any of the following compounds can be used:

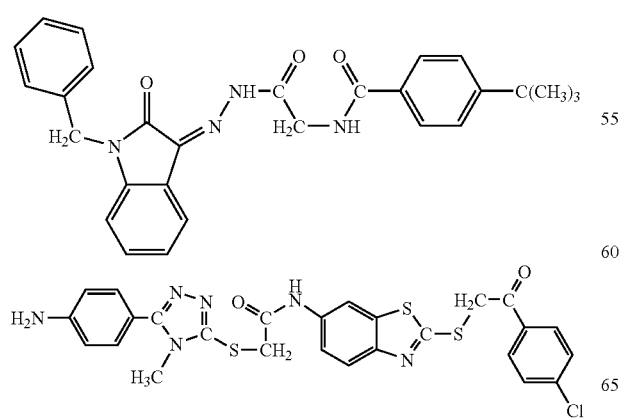

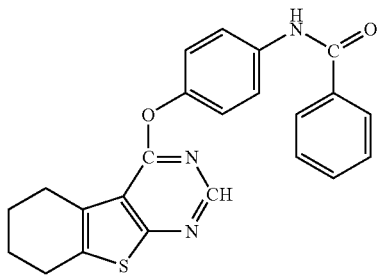

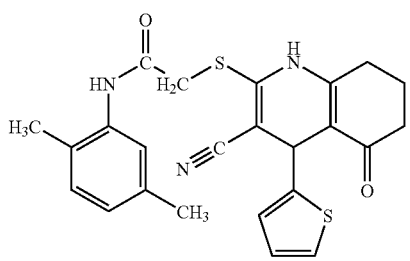

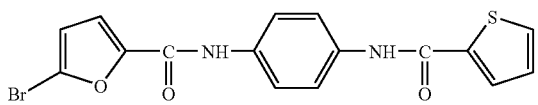

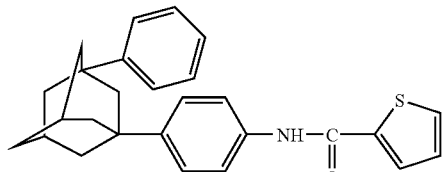

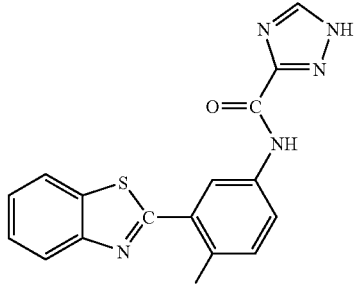

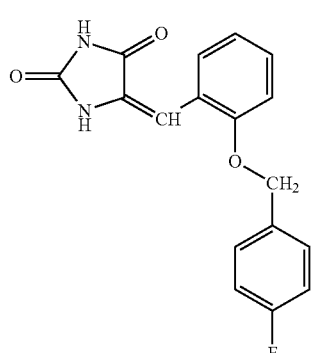

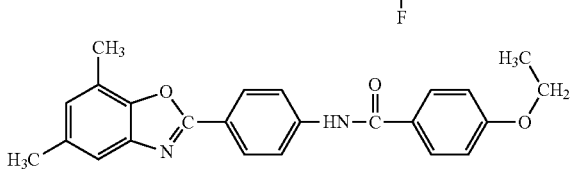

7
-continued
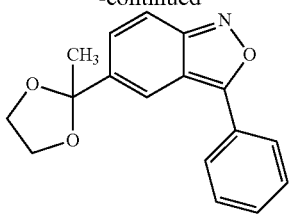
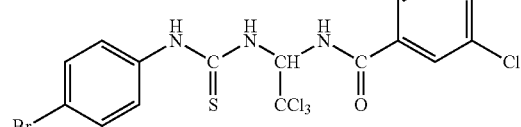
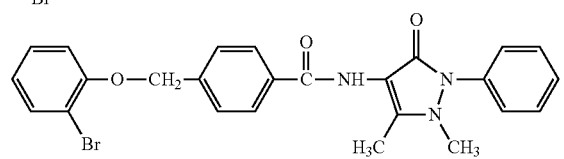
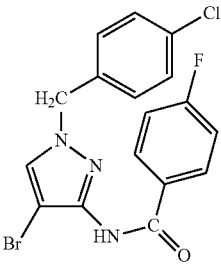
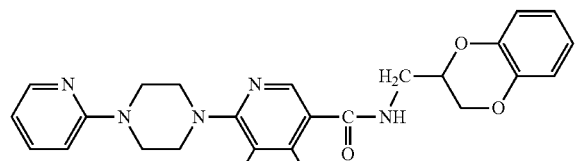
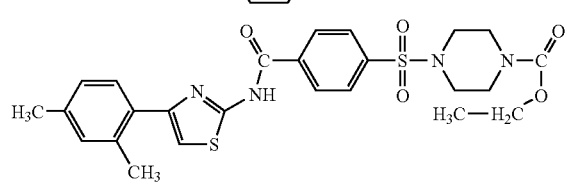
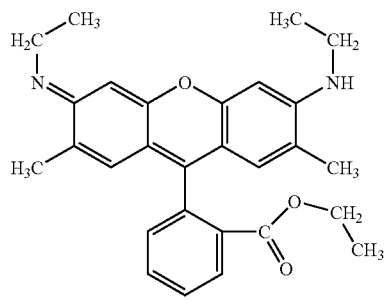
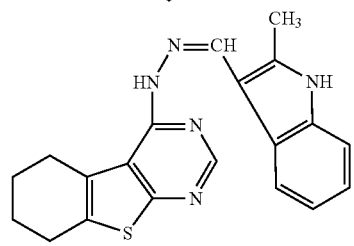
8
-continued
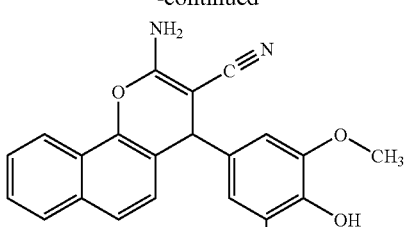
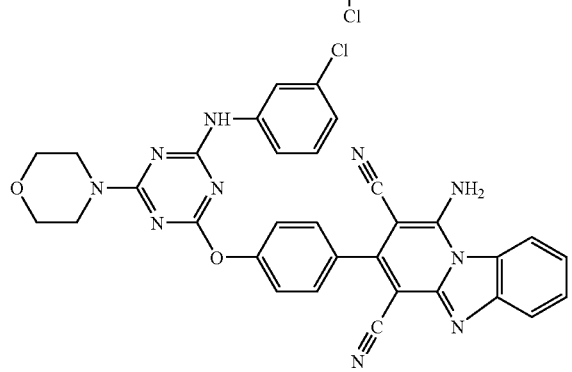
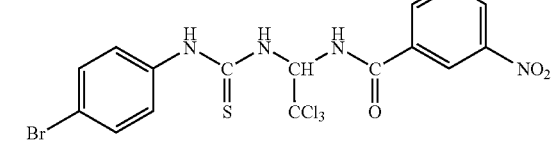
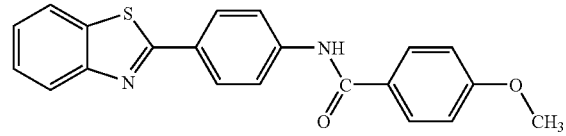
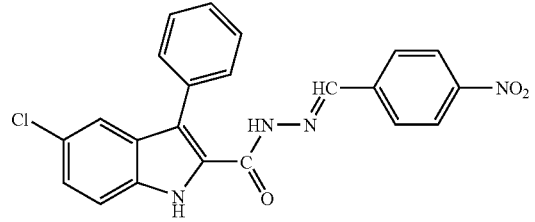
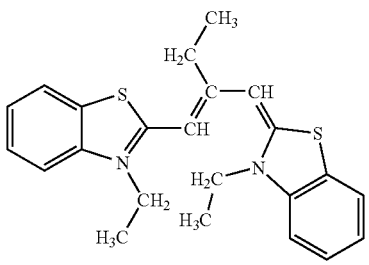
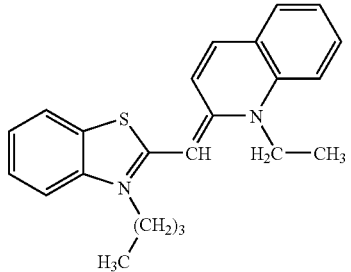

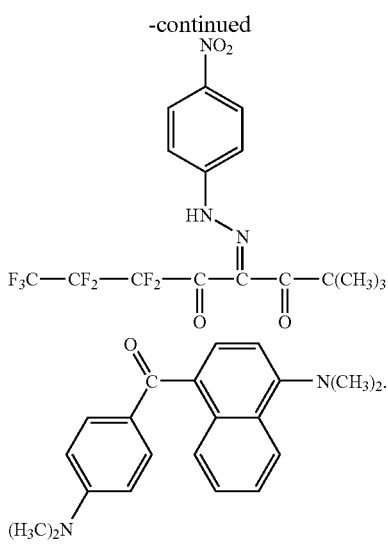

According to one embodiment of the invention, a compound is provided, the compound comprising an alkylpyridyl moiety bridged to a benzamide moiety, wherein the benzamide moiety includes a first substituent attached to the benzamide moiety via the nitrogen atom of the benzamide moiety.

According to another embodiment of the invention, a compound is provided, the compound comprising two benzamide moieties connected with a phenylene bridge.

According to yet another embodiment of the invention, a compound is provided, the compound comprising a first heterocyclic ring fused with a second heterocyclic ring, where the first ring is a substituted 1,3-diazine-6-one, and the second ring is selected from an N-substituted thiazole-2-thione and a substituted thiophene.

According to another embodiment of the invention, a compound is provided, the compound comprising a thiazole moiety carrying a heterocyclic substituent and a secondary amino substituent, where the heterocyclic substituent is selected from thiazolyl and pyridyl and the secondary amino substitutent is ethoxyphenylene group.

According to another embodiment of the invention, a compound is provided, the compound comprising phtalazine moiety carrying at least two substitutents, where the first substitutent includes a substituted phenyl or benzyl group, and the second substitutent includes a secondary aromatic amino group.

According to another embodiment of the invention, a compound is provided, the compound comprising a substituted chromone moiety carrying at least two substitutents, where the first substitutent includes a substituted phenyl or phenoxy group, and the second substitutent includes an aromatic ester group.

According to another embodiment of the invention, a compound is provided, the compound comprising a substituted benzoxazole moiety carrying at least two substitutents, where the first substitutent is selected from a substituted phenyl group and a substituted benzamido group, and the second substitutent is selected from a substituted phenyl group and a substituted furylamido group.

According to another embodiment of the invention, a compound is provided, the compound comprising a phenylquinazoline moiety and a substitutent, where the substitutent is selected from a secondary aromatic amino group and an anyline moiety.

According to another embodiment of the invention, a compound is provided, the compound comprising a thiazole moiety bridged to a substituted pyrrole-pyridine moiety.

According to another embodiment of the invention, a method for treating a disorder is provided, the method includes administering an effective amount of a compound according to any embodiment of the present invention, or any combination thereof, or pharmaceutically acceptable salts, hydrates, solvates, crystal forms and individual diastereomers thereof, to a subject in need of such treatment. The compound can be administered in combination with a therapeutic agent, immunomodulatory agent, therapeutic antibody or an enzyme inhibitor.

Thus, in one embodiment, the methods of the present invention include the use of aromatic compounds that agonize ptc inhibition of hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells that are provided in culture (in vitro), or on cells in a whole animal (in vivo).

In another embodiment of the invention, the subject method can be used to treat epithelial cells having a phenotype of ptc loss-of-function, hedgehog gain-of-function, or smoothened gain-of-function. For instance, the subject method can be used in treating or preventing basal cell carcinoma or other hedgehog pathway-related disorders. In certain embodiments, a subject antagonist may inhibit activation of a hedgehog pathway by binding to smoothened.

In another embodiment, the subject method can be used as part of a treatment regimen for malignant medulloblastoma and other primary CNS malignant neuroectodermal tumors. In other embodiments, the subject method can be used as part of a treatment regimen for rhabdomyosarcoma, lung cancer, and in particular small cell lung cancer, gut-derived tumors, including but not limited to cancer of the esophagus, stomach, pancreas, and biliary duct system, or prostatic and bladder cancers.

In another aspect, the present invention provides pharmaceutical preparations comprising, as an active ingredient, a hedgehog antagonist, ptc agonist, or smoothened antagonist such as described herein, formulated in an amount sufficient to inhibit, in vivo, proliferation or other biological consequences of ptc loss-of-function, hedgehog gain-of-function, or smoothened gain-of-function.

The subject treatments using hedgehog antagonists, patched agonists, or smoothened antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

According to another embodiment of the invention, a pharmaceutical composition is provided. The composition can include a compound according to any embodiment of the present invention, or any combination thereof, in a pharmaceutically acceptable carrier.

According to another embodiment of the invention, an article of manufacture is provided, the article comprising packaging material and a pharmaceutical composition contained within the packaging material, where the packaging material comprises a label which indicates that the pharmaceutical composition can be used for treatment of disorders and where the pharmaceutical composition can include a compound according to any embodiment of the present invention, or any combination thereof, in a pharmaceutically acceptable carrier.

According to another embodiment of the invention, a process for making a pharmaceutical composition is provided, the method comprising combining a compound according to any embodiment of the present invention, or any combination thereof, or its pharmaceutically acceptable salts, hydrates, solvates, crystal forms salts and individual diastereomers thereof, and a pharmaceutically acceptable carrier.

According to another embodiment, the compounds of the invention are divided into classes based on structure, and are all effective in antagonizing the hedgehog pathway, as indicated by the $IC_{50}$ for pathway inhibition. Other compounds related in structure to those disclosed herein are also anticipated to have potency in pathway inhibition, and are included as part of the invention.

DETAILED DESCRIPTION OF THE INVENTION

The present invention relates to the discovery that signal transduction pathways, such as the Hedgehog pathway, regulated by hedgehog, patched (ptc), and/or smoothened can be inhibited, at least in part, by aromatic compounds. As set out in more detail below, groups of aromatic compounds inhibit proliferation of normal cells or tumor cells having a patched loss-of-function phenotype, a hedgehog gain-of-function phenotype, or a smoothened gain-of-function phenotype.

While not wishing to be bound by any particular theory, the activation of a receptor may be the mechanism by which these compounds act. For example, the ability of these compounds to inhibit proliferation of patched loss-of-function ($ptc^{lof}$) cells may be due to the ability of such molecules to interact with hedgehog, patched, or smoothened, or at least to interfere with the ability of those proteins to activate a hedgehog, ptc, and/or smoothened-mediated signal transduction pathway. Signal transduction antagonists of different structures, even ones that bind to the same protein in the signaling pathways, may act in slightly different ways. Accordingly, even if a particular condition caused, or contributed to, by aberrant or unwanted activation of the hedgehog pathway shows little response to treatment by one of the antagonists disclosed herein, another of the antagonists disclosed herein may nonetheless be efficacious.

It is, therefore, specifically contemplated that these aromatic compounds that interfere with aspects of hedgehog, ptc, or smoothened signal transduction activity will likewise be capable of inhibiting proliferation (or other biological consequences) in normal cells and/or cells having a patched loss-of-function phenotype, a hedgehog gain-of-function phenotype, or a smoothened gain-of-function phenotype. Thus, it is contemplated that in certain embodiments, these compounds may be useful for inhibiting hedgehog activity in normal cells, e.g., those that do not have a genetic mutation that activates the hedgehog pathway. In these embodiments, the subject inhibitors are organic molecules having a molecular weight less than 2500 amu, more preferably less than 1500 amu, and even more preferably less than 750 amu, and are capable of inhibiting at least some of the biological activities of hedgehog, e.g. Hh, Shh, Ihh, Dhh, specifically in target cells.

Thus, the methods of the present invention include the use of compounds, such as aromatic compounds, which antagonize activity of the hedgehog pathway resulting in the regulation of repair and/or functional performance of a wide range of cells, tissues, and organs having the phenotype of ptc loss-of-function, hedgehog gain-of-function, or smoothened gain-of-function. In an alternative embodiment, the present invention provides compounds, such as aromatic compounds, which agonize activity of the hedgehog pathway, resulting in the regulation, of repair and/or functional performance of a wide range of cells, tissues, and organs having the phenotype of ptc gain-of-function, hedgehog loss-of-function, or smoothened loss-of-function. For instance, the subject methods have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In an embodiment, the subject method can be to treat epithelial cells having a phenotype of ptc loss-of-function, hedgehog gain-of-function, or smoothened gain-of-function employing a compound, such as an aromatic compound, which antagonizes hedgehog function, e.g., by agonizing hedgehog, patched, or smoothened activity. For instance, the subject method can be used in treating or preventing basal cell carcinoma or other hedgehog pathway-related disorders. In an alternative embodiment, the subject method can be to treat epithelial cells having a phenotype of ptc gain-of-function, hedgehog loss-of-function, or smoothened loss-of-function employing an agent which agonizes hedgehog function, e.g., by antagonizing hedgehog, patched, or smoothened activity.

In another embodiment, the subject method can be used as part of a treatment regimen for cancer. Such cancers include malignant medulloblastoma and other primary CNS malignant neuroectodermal tumors, rhabdomyosarcoma, lung cancer, and in particular small cell lung cancer, gut-derived tumors, including but not limited to cancer of the esophagus, stomach, pancreas, and biliary duct system, or prostatic and bladder cancers.

In another aspect, the present invention provides pharmaceutical preparations comprising, an aromatic compound such as described herein, formulated in an amount sufficient to regulate, in vivo, the hedgehog pathway, e.g., proliferation or other biological consequences of mis-expression of ptc, hedgehog, or smoothened.

The subject treatments using the subject compounds can be effective for both human and animal subjects. Animal subjects to which the invention is applicable extend to both domestic animals and livestock, raised either as pets or for commercial purposes. Examples are dogs, cats, cattle, horses, sheep, hogs, and goats.

The following terminology and definitions apply as used in the present application. The chemical terms are generally used in conformity with the terminology recommended by the International Union of Pure and Applied Chemistry (IUPAC).

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, "mis-expression" of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "agonist" refers to an agent or analog that binds productively to a receptor and mimics its biological activity. The term "antagonist" refers to an agent that binds to receptors but does not provoke the normal biological response. Thus, an antagonist potentiates or recapitulates, for example, the bioactivity of patched, such as to repress transcription of target genes. The antagonists can be used to overcome a ptc loss-of-function and/or a smoothened gain-of-function, the latter also being referred to as 'smoothened antagonists'. The term 'hedgehog antagonist' as used herein refers not only to any agent that may act by directly inhibiting the normal function of the hedgehog protein, but also to any agent that inhibits the hedgehog signaling pathway, and thus recapitulates the function of ptc. The term 'hedgehog agonist' likewise refers to an agent which antagonizes or blocks the bioactivity of patched, such as to increase transcription of target genes. The hedgehog antagonists can be used to overcome a ptc gain-of-function and/or a smoothened loss-of-function, the latter also being referred to as 'smoothened agonists'.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The "gain-of-function" may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell. 'Hedgehog loss-of-function' refers to the direct opposite of a hedgehog gain-of-function, e.g., an aberrant modification or mutation that results in a phenotype which resembles contacting a cell with an agent which blocks hedgehog function.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The 'gain-of-function' may include a loss of the ability of the ptc gene product to regulate the level of expression of Ci genes, e.g., Gli1, Gli2 and Gli3.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

The term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

The term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "smoothened gain-of-function" refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., Nature 384: 177-179 (1996)). The smo gene is a segment-polarity gene required for the correct patterning of every segment in Drosophila (Alcedo et al., Cell 86: 221-232 (1996)). Human homologs of smo have been identified. See, for example, Stone et al., Nature 384:129-134 (1996), and GenBank accession no. U84401. The smoothened gene encodes an integral membrane protein with characteristics of heterotrimeric G-protein-coupled receptors; i.e., 7-trans-membrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, Nature 384: 119-120 (1996)). Rather, the binding of Sonic hedgehog (SHH) to its receptor, PTCH, is thought to prevent normal inhibition by PTCH of smoothened (SMO), a seven-span transmembrane protein.

The term "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "heterocyclic," when used to describe an aromatic ring, means that the aromatic ring contains at least one heteroatom. The abbreviation "Het" is sometimes used to signify a heterocyclic structure.

The term "heteroatom" is defined to include any atom other than carbon, for example, N, O, or S.

The term "aromatic" or "aryl" is defined to include a cyclically conjugated molecular entity with a stability, due to delocalization, significantly greater than that of a hypothetical localized structure, such as the Kekulé structure.

The term "heterocyclic," when not used to describe an aromatic ring, is defined to include cyclic (i.e., ring-containing) groups other than aromatic groups, the cyclic group being formed by between 3 and about 14 carbon atoms and at least one heteroatom described above. The term "substituted heterocyclic" is defined to include both aromatic and non-aromatic structures to heterocyclic groups further bearing one or more substituents.

The term "heteroaryl" is defined to include aromatic rings, where the ring structure is formed by between 3 and about 14 carbon atoms and by at least one heteroatom described above, and the term "substituted heteroaryl" refers to heteroaryl groups further bearing one or more substituents.

The term "fused rings" is defined as polycyclic ring system in which any two adjacent rings have at least two adjacent atoms in common.

The term "bridge" is defined as intramolecular connection between two separate aromatic structures. Examples of a bridge include a single-bond and a heteroatom, e.g., oxygen or sulfur atoms.

The term "alkyl" is defined to include a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like.

The term "methoxy" is defined as the group —OCH$_3$.

The term "ethoxy" is defined as the group —OCH$_2$—CH$_3$.

The term "halogen" is defined to include an atom of fluorine, chlorine, bromine or iodine.

The term "amino" or "amino group" is defined to include moieties —NRR', where each of R and R' is hydrogen ("primary amino"), or one of them is an organic radical ("secondary amino"), or each is an organic radical ("tertiary amino"); if either R or R' is an aromatic group, the amino group is defined as "secondary aromatic amino" group.

The term "aminoalkyl" or "aminoalkyl group" is defined to include moieties —R—N(R'R"), wherein R is an organic radical and each of R' and R" is hydrogen or an organic radical. If at least one of R' and R" is an organic radical, the moiety is defined as "alkylaminoalkyl" or "alkylaminoalkyl group."

The term "sulfonyl" or "sulfonyl group" is defined to include moieties that comprise structure (S), in which R is an organic radical:

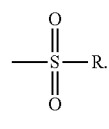
(S)

The term "sulfonylamino" or "sulfonylamino group" is defined to include moieties that comprise structure (SA), in which R is an organic radical:

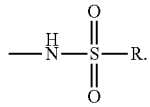
(Sa)

The term "amide," or "amido," or "amide group," or "amido group" is defined to include moieties containing at least one acyl group >C=O attached to nitrogen. The term "substituted amide" is defined to include moieties containing a structure RNH—CO—, in which R is an organic radical.

The term "benzamide" or "benzamido" is defined as an amido derivative of benzoic acid, and having structure (Bza):

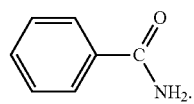
(Bza)

The term "N-substituted benzamide" is defined as a benzamide where at least one hydrogen in the amino group is substituted with a radical R(N-Bza):

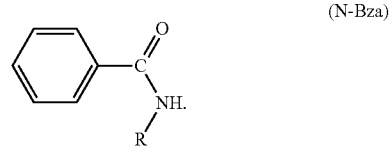
(N-Bza)

The term "phenyl" is defined to include moieties having structure (Ph):

(Ph)

The term "phenylene" is defined to include moieties having structure (Phl):

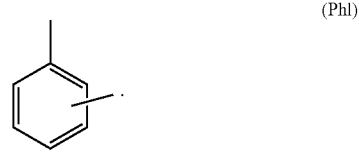
(Phl)

The term "ethoxyphenylene" is defined to include moieties comprising phenyl group and ethoxy group attached to the phenyl ring (Ephl):

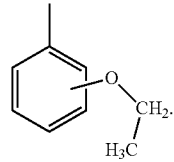
(Ephl)

The term "pyridyl" is defined to include moieties containing a radical derived from pyridine. The structure of pyridyl is shown as the structure (Py):

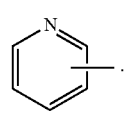
(Py)

The term "alkylpyridyl" is defined to include moieties containing a radical derived from pyridine, and further including an alkyl substitutent R in the pyridine ring. The structure of alkylpyridyl is shown as the structure (Apy):

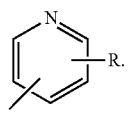
(Apy)

The term "diazine" is defined as a heterocyclic structure (Dz):

(Dz)

The term "1,3-diazine-6-one" is defined as a heterocyclic structure (Dzo) comprising a diazine moiety and ketone group:

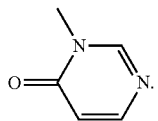
(Dzo)

The term "thiazole" is defined as a heterocyclic structure (Tz):

(Tz)

The term "thiazolyl" is defined to include moieties containing a radical derived from thiazole. The structure of thiazolyl is shown as the structure (Tzy):

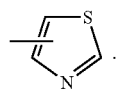
(Tzy)

The term "amino-substituted thiazole" is defined as thiazole further including a primary or secondary amino group connected to the thiazole ring.

The term "thiazole-2-thione" is defined as a heterocyclic structure (Tzo) comprising a thiazole moiety and thioketone moiety:

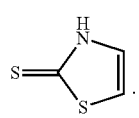
(Tzo)

The term "thiophene" is defined as a 5-member heterocycle containing sulfur (TPh):

(Tph)

The term "phtalazine" is defined as the heterocyclic structure (Pht):

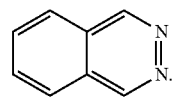
(Pht)

The term "chromone" is defined as the heterocyclic structure (Chr):

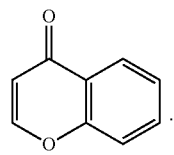
(Chr)

The term "benzoxazole" is defined as the heterocyclic structure (Box):

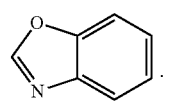
(Box)

The term "furyl" is defined to include moieties containing a radical derived from furan. The structure of furyl is shown as the structure (Fy):

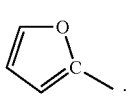
(Fy)

The term "furylamido" is defined as a furyl having an amide group connected to the furan ring.

The term "quinazoline" is defined as the heterocyclic structure (Qaz):

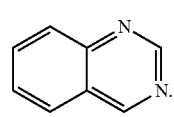
(Qaz)

The term "pyrrole-pyridine" is defined as the heterocyclic structure (Ppy):

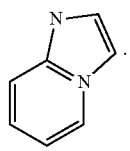
(Ppy)

The term "effective amount" is defined as the amount of a compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality. For example, a "therapeutically effective amount" of, e.g., an aromatic compound, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The term "pharmaceutically acceptable" is defined as a carrier, whether diluent or excipient, that is compatible with the other ingredients of the formulation and not deleterious to the recipient thereof.

The terms "administration of a compound" or "administering a compound" is defined to include an act of providing a compound of the invention or pharmaceutical composition to the subject in need of treatment.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit signal transduction pathways), wherein one or more simple variations of substituents are made which do not adversely affect the efficacy of the compound. In general, the compounds of the present invention may be prepared by the methods known in the art, using readily available starting materials, reagents and conventional synthesis procedures. In these methods, it is also possible to make use of variants which are in themselves known, but are not mentioned here.

As described in further detail below, it is contemplated that the subject methods can be carried out using a variety of different aromatic compounds, which can be readily identified, e.g., by such drug screening assays as described herein.

According to an embodiment of the invention, a first type of compound is provided for treatment of various diseases, disorders, and pathologies. The compounds of the first type can include an alkylpyridyl moiety bridged to a benzamide moiety, where the benzamide moiety can include a first substitutent attached to the benzamide moiety via the nitrogen atom of the benzamide moiety. The first substitutent can comprise an aryl structure which can include at least one second substitutent, where the second substitutent can be an unsubstituted or substituted alkyl, a halogen, an alkoxy, acetyl, or nitro.

Compounds of the first type can be described as compounds having the general structure (I), or a pharmaceutically acceptable salt thereof:

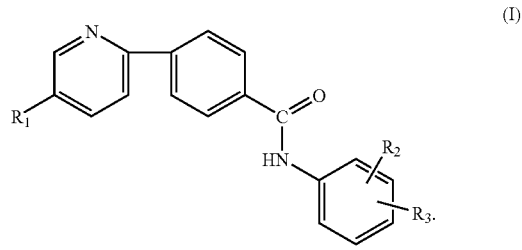
(I)

In structure (I), $R_1$ can be an alkyl, for example, ethyl, n-propyl or n-amyl; $R_2$ can be hydrogen, an alkyl (e.g., methyl), halogen (e.g., chlorine), or an alkoxy group (e.g., methoxy); and $R_3$ can be an unsubstituted or substituted alkyl group (e.g., methyl or trifluoromethyl), halogen (e.g., chlorine or iodine), an alkoxy group (e.g., methoxy), acetyl group, or nitro group.

Some examples of particular compounds described by the general structure (I) include compounds having the formulae (1)-(7):

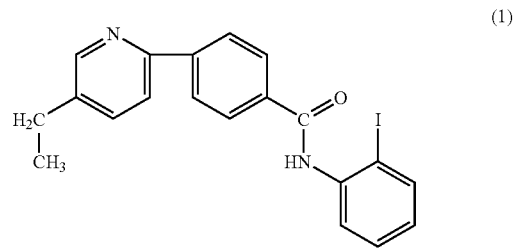
(1)

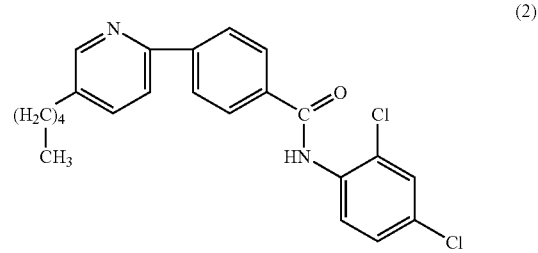
(2)

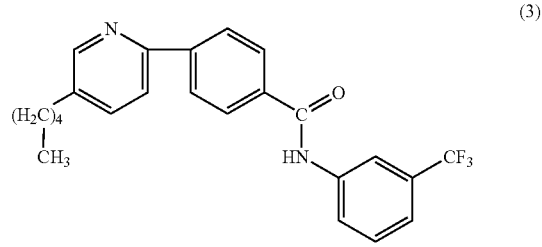
(3)

-continued (4)
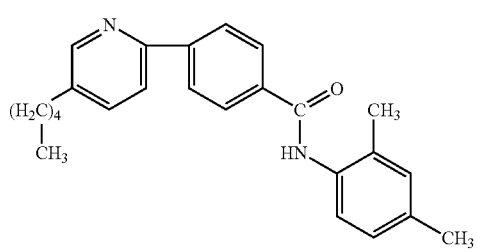

(5)
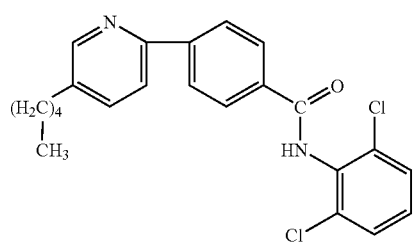

(6)
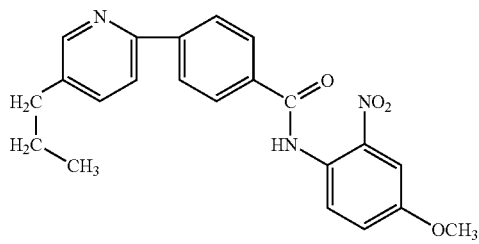

(7)
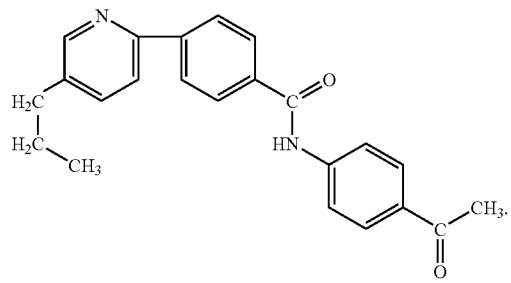

According to an embodiment of the invention, a second type of compounds is provided for treatment of various diseases, disorders, and pathologies. The compounds of the second type can include two benzamide moieties connected with a phenylene bridge, for example, the 1,3-phenylene bridge. The benzamide moieties can include a substitutent, such as tert-butyl, chlorine, bromine, or nitro.

Compounds of the second type can be described as compounds having the general structure (II), or a pharmaceutically acceptable salt thereof:

(II)
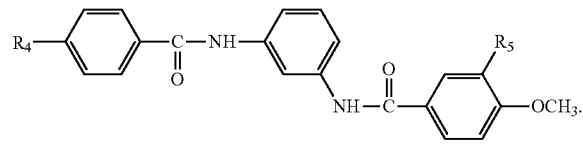

In structure (II), $R_4$ can be tert-butyl or chlorine, and $R_5$ can be nitro group or bromine.

Some examples of particular compounds described by the general structure (II) include compounds having the formulae (8) or (9):

(8)
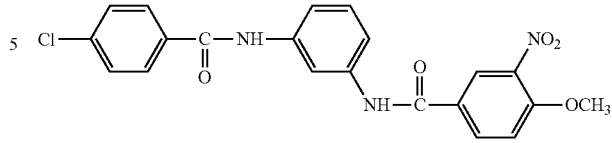

(9)
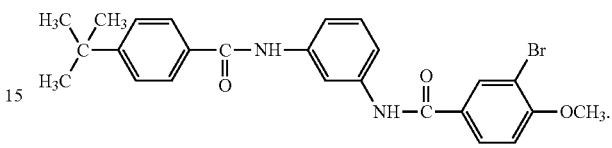

According to an embodiment of the invention, a third type of compounds is provided for treatment of various diseases, disorders, and pathologies. The compounds of the third type can include a first heterocyclic ring fused with a second heterocyclic ring, where the first ring can be 1,3-diazine-6-one, and the second ring can be N-substituted thiazole-2-thione or a substituted thiophene.

Compounds of the third type can be described as compounds having either the general structure (III), or the general structure (IV), or a pharmaceutically acceptable salt thereof:

(III)
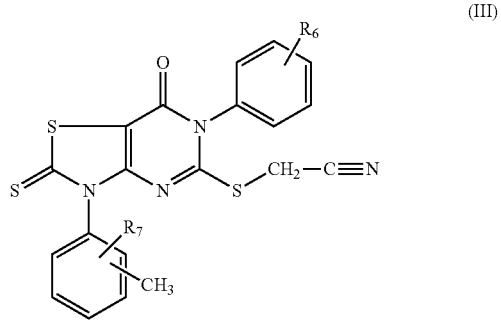

(IV)
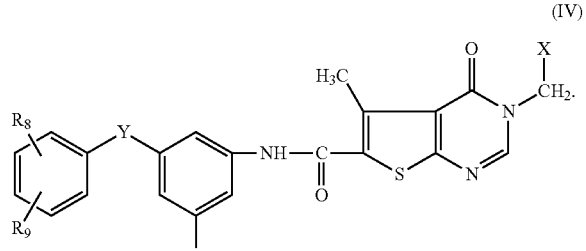

In structure (III), $R_6$ can be methyl or ethoxy group, and $R_7$ can be hydrogen or methyl. In structure (IV), $R_8$ can be hydrogen or methyl, $R_9$ can be hydrogen, chlorine or fluorine, X can be ethyl or fluorophenyl, and Y can be an atom of oxygen or sulfur. Some examples of particular compounds described by the general structure (III) include compounds having the formulae (10) and (11), and some examples of particular compounds described by the general structure (IV) include compounds having the formulae having the formulae (12)-(15):

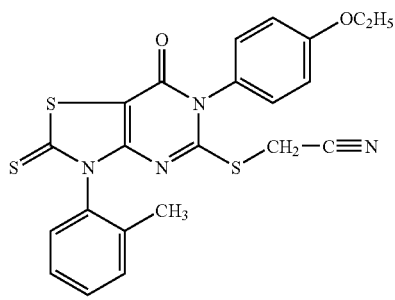

(10)

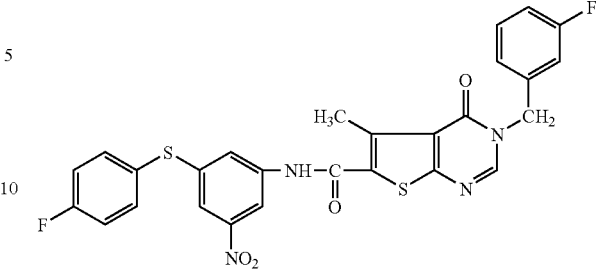

(15)

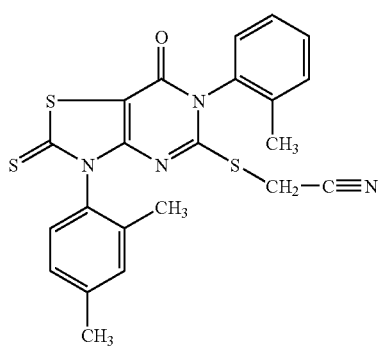

(11)

According to an embodiment of the invention, a fourth type of compounds is provided for treatment of various diseases, disorders, and pathologies. The compounds of the fourth type can include a thiazole moiety carrying a heterocyclic substitutent and a secondary amino substitutent, where the heterocyclic substitutent can be thiazolyl or pyridyl, and the secondary amino substitutent can be ethoxyphenylene group.

Compounds of the fourth type can be described as compounds having the general structure (V), or a pharmaceutically acceptable salt thereof:

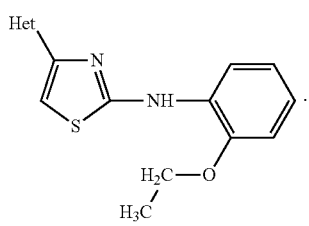

(V)

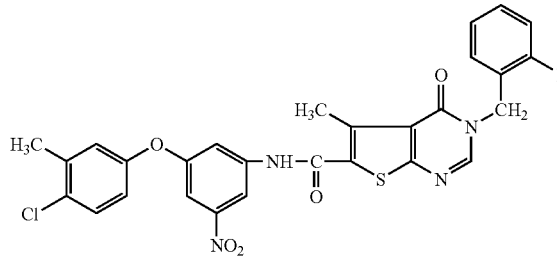

(12)

In structure (V), Het is a heterocyclic radical, for example, pyridyl or thiazolyl. Some examples of particular compounds described by the general structure (V) include compounds having the formulae having the formulae (16) or (17):

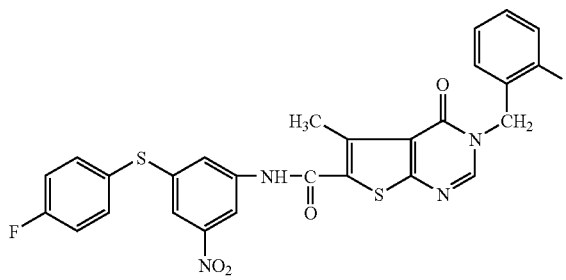

(13)

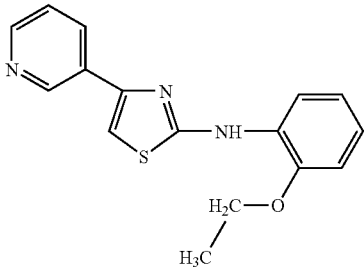

(16)

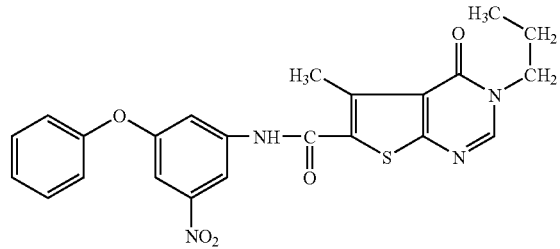

(14)

According to an embodiment of the invention, a fifth type of compounds is provided for treatment of various diseases, disorders, and pathologies. The compounds of the fifth type can include a phtalazine moiety carrying at least two substitutents, where the first substitutent can include a substituted phenyl or benzyl group, and the second substitutent can include a secondary aromatic amino group.

Compounds of the fifth type can be described as compounds having the general structure (VI), or a pharmaceutically acceptable salt thereof:

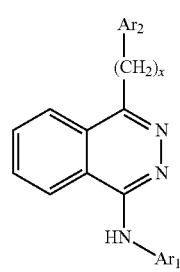
(VI)

In structure (VI), $Ar_1$ can be any of aromatic moieties:

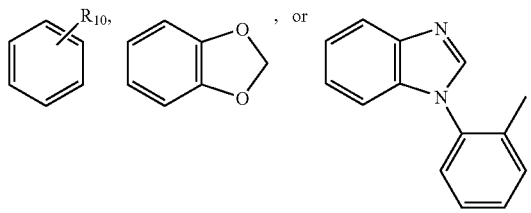

$Ar_2$ can be an aromatic moiety having the structure:

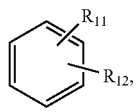

$R_{10}$ can be methyl or chlorine, $R_{11}$ can be hydrogen, methyl, or chlorine, and $R_{12}$ can be any of hydrogen,

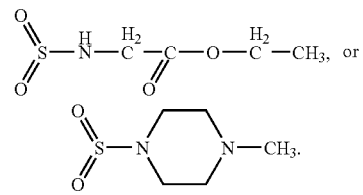

Some examples of particular compounds described by the general structure (VI) include compounds having the formulae (18)-(24):

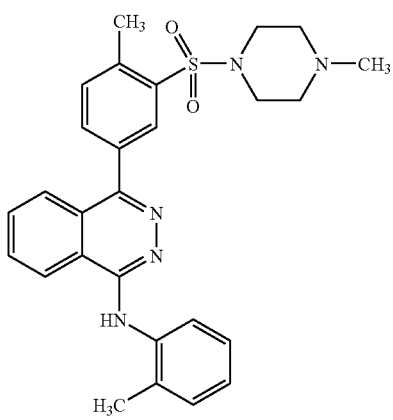
(18)

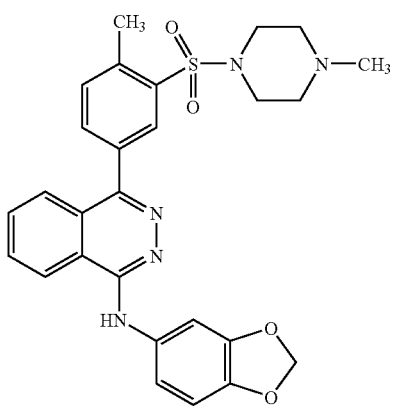
(19)

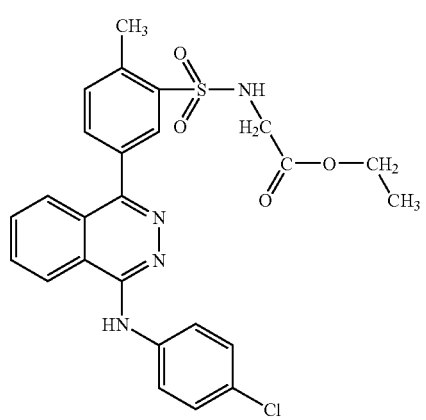
(20)

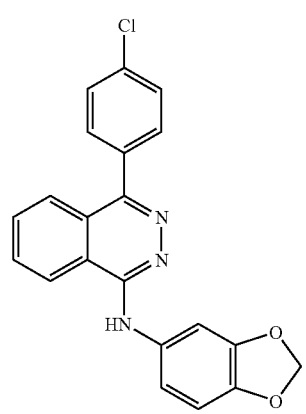
(21)

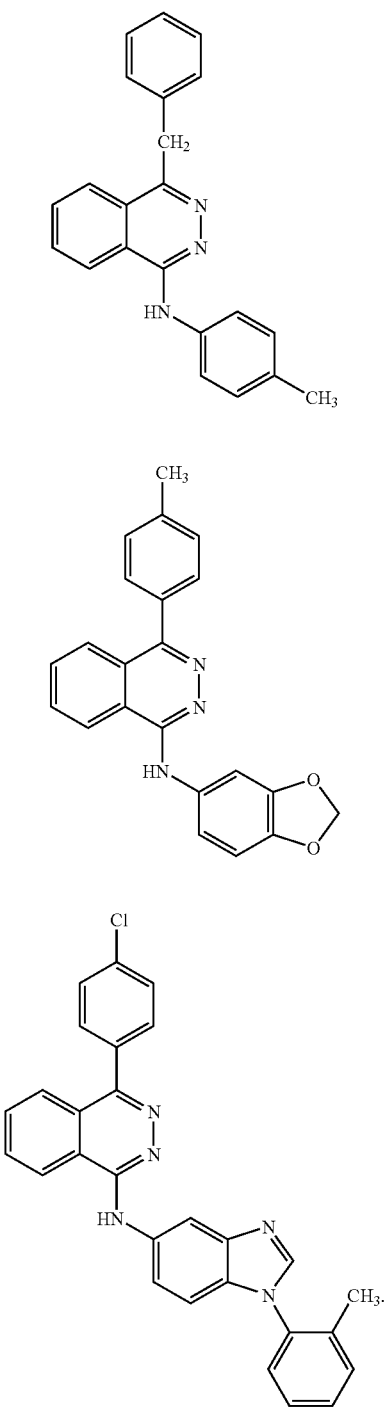

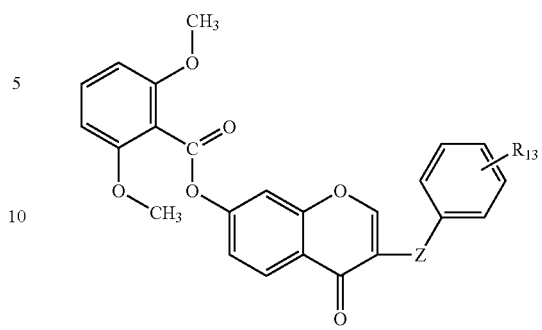

In structure (VII), $R_{13}$ can include chlorine, bromine, or methoxy, and Z can include at atom of oxygen or a single σ-bond. Some examples of particular compounds described by the general structure (VII) include compounds having the formulae (25)-(27):

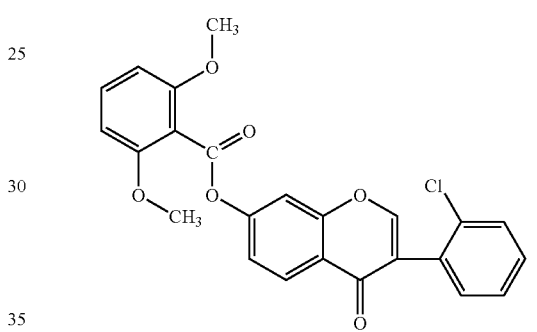

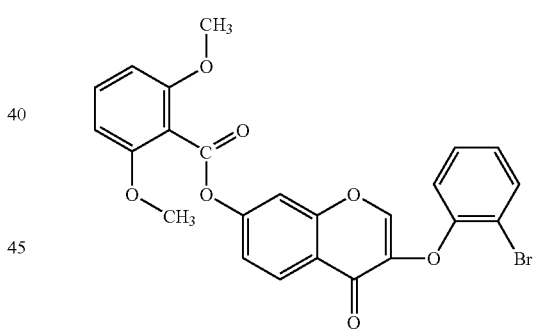

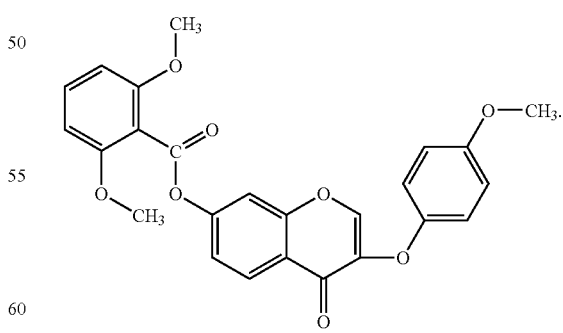

According to an embodiment of the invention, a sixth type of compounds is provided for treatment of various diseases, disorders, and pathologies. The compounds of the sixth type can include a substituted chromone moiety carrying at least two substitutents, where the first substitutent can include a substituted phenyl or phenoxy group, and the second substitutent can include an aromatic ester group.

Compounds of the sixth type can be described as compounds having the general structure (VII), or a pharmaceutically acceptable salt thereof:

According to an embodiment of the invention, a seventh type of compounds is provided for treatment of various diseases, disorders, and pathologies. The compounds of the seventh type can include a substituted benzoxazole moiety carrying at least two substitutents, where the first substitutent can include a substituted phenyl group or a substituted benzamido group, and the second substitutent can include a substituted phenyl group or a substituted furylamido group.

Compounds of the seventh type can be described as compounds having the general structure (VIII), or a pharmaceutically acceptable salt thereof:

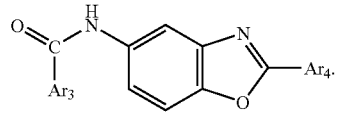
(VIII)

In structure (VIII), Ar₃ can be any of aromatic moieties:

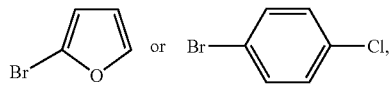

Ar₄ can be an aromatic moiety:

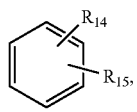

R₁₄ can include hydrogen or bromine, and R₁₅ can include tert-butyl or iodine. Some examples of particular compounds described by the general structure (VIII) include compounds having the formulae (28) or (29):

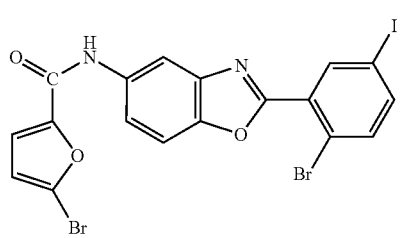
(28)

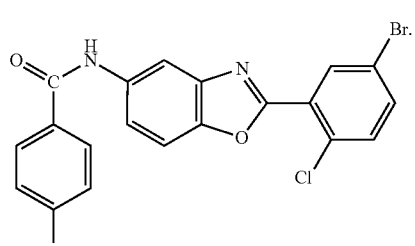
(29)

According to an embodiment of the invention, an eighth type of compounds is provided for treatment of various diseases, disorders, and pathologies. The compounds of the eighth type can include a phenylquinazoline moiety and a substitutent, where the substitutent can include a secondary aromatic amino group or an anyline moiety.

Compounds of the eighth type can be described as compounds having the general structure (IX), or a pharmaceutically acceptable salt thereof:

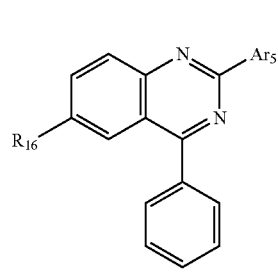
(IX)

In structure (IX), Ar₅ can be any of aromatic moieties:

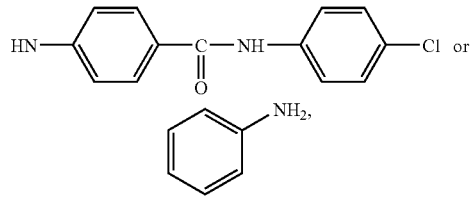

and R₁₆ can be hydrogen or methyl. Some examples of particular compounds described by the general structure (IX) include compounds having the formulae (30) or (31):

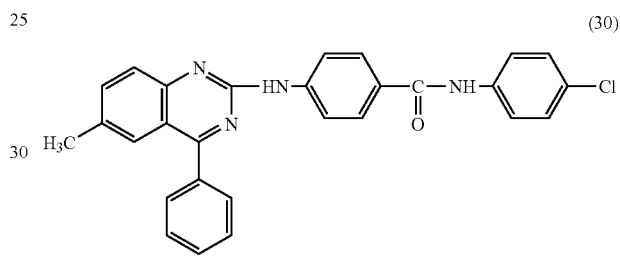
(30)

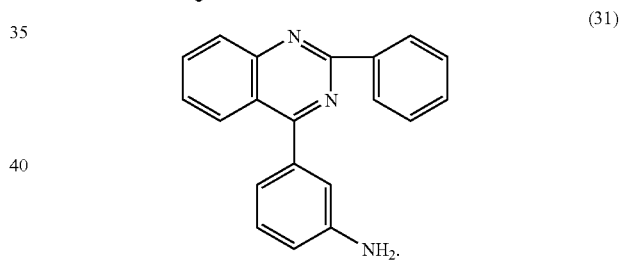
(31)

According to an embodiment of the invention, a ninth type of compounds is provided for treatment of various diseases, disorders, and pathologies. The compounds of the ninth type can include a thiazole moiety bridged to a substituted pyrrole-pyridine moiety. The thiazole moiety can further include a secondary aromatic amino group.

Compounds of the ninth type can be described as compounds having the general structure (X), or a pharmaceutically acceptable salt thereof:

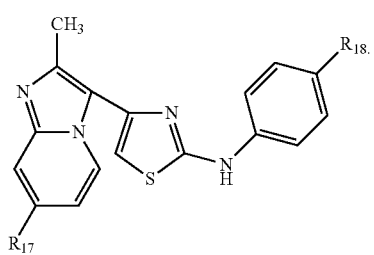
(X)

In structure (X), $R_{17}$ can be hydrogen or methyl, and $R_{18}$ can be any of methyl, methoxy, or ethoxy. Some examples of particular compounds described by the general structure (X) include compounds having the formulae (32)-(34):
(32)
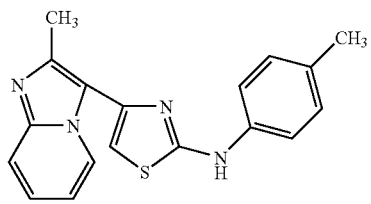
(33)
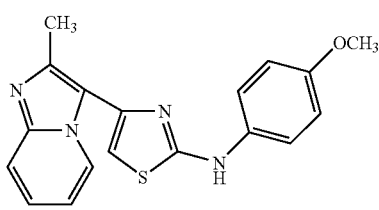
(34)
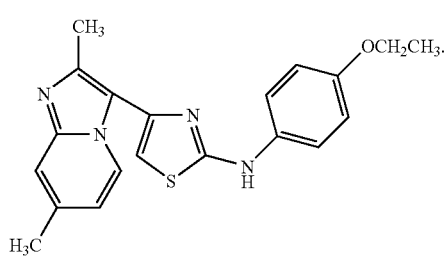
According to an embodiment of the invention, compounds having formulae (35)-(60) are provided for treatment of various diseases, disorders, and pathologies.
(35)
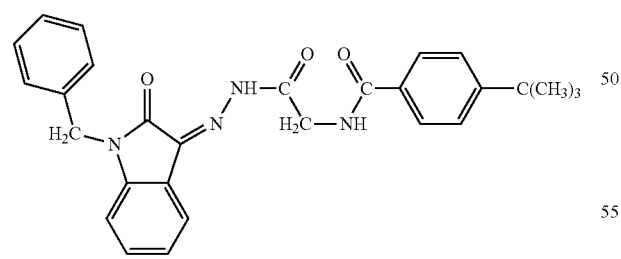
(36)
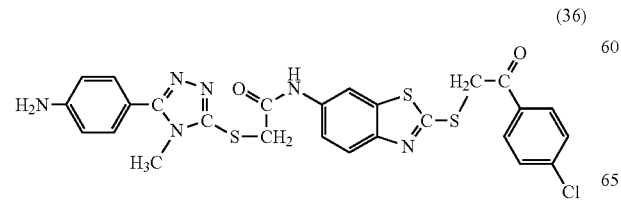
(37)
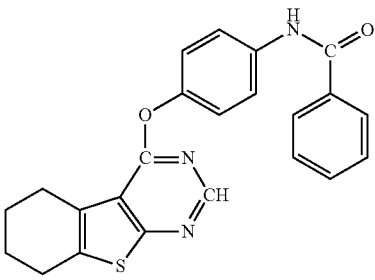
(38)
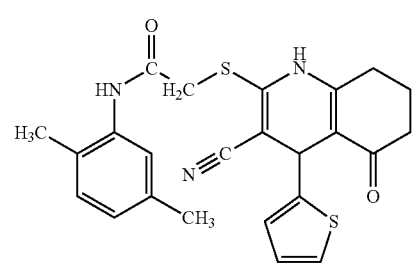
(39)
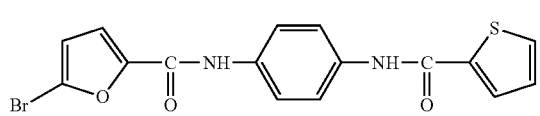
(40)
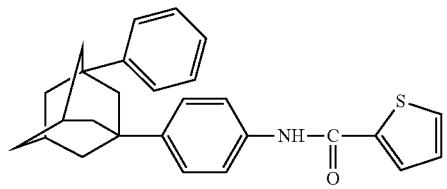
(41)
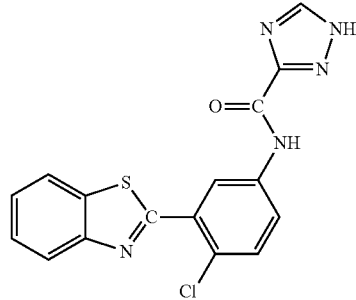
(42)
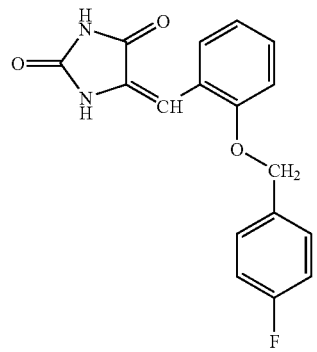

(43) 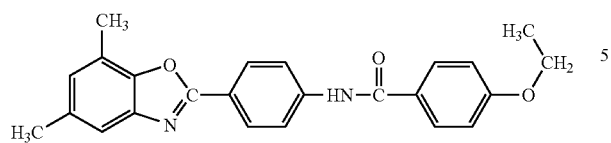
(44) 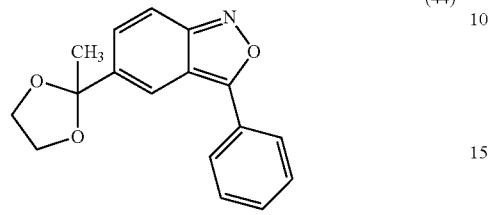
(45) 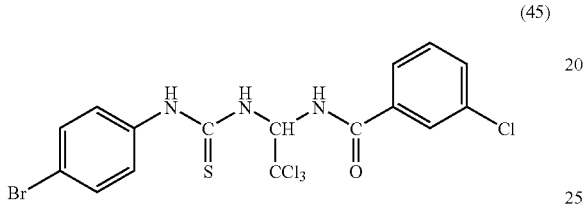
(46) 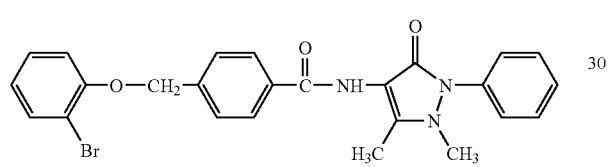
(47) 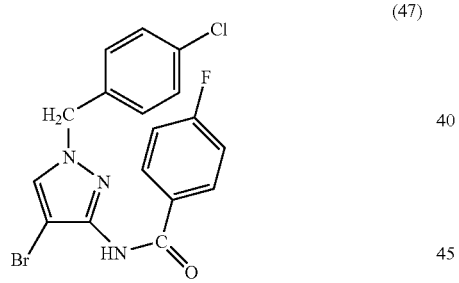
(48) 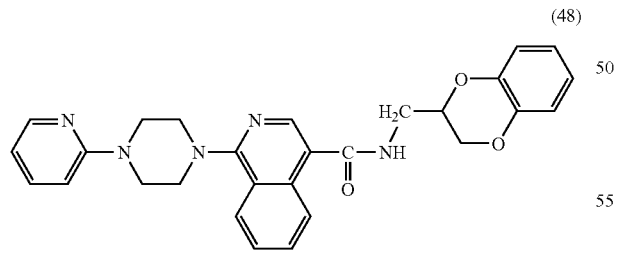
(49) 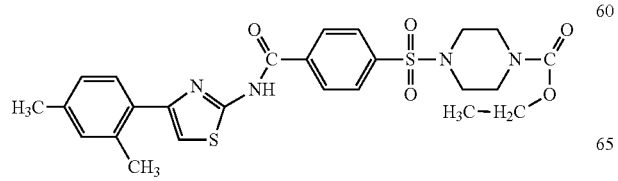
(50) 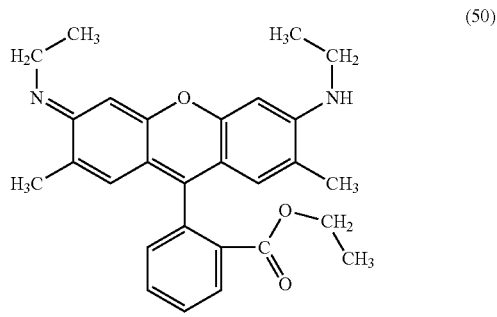
(51) 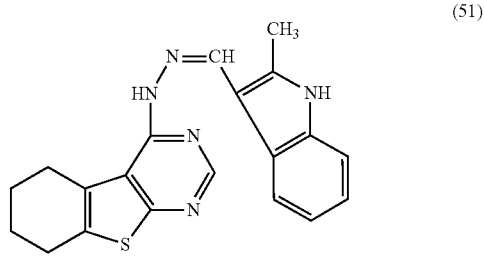
(52) 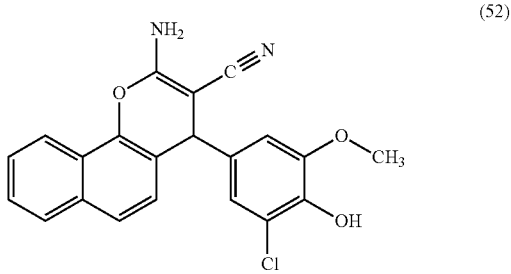
(53) 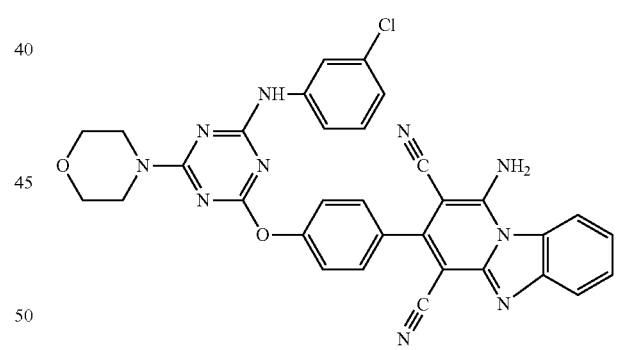
(54) 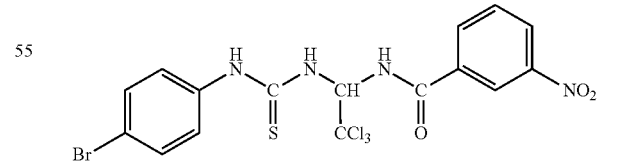
(55) 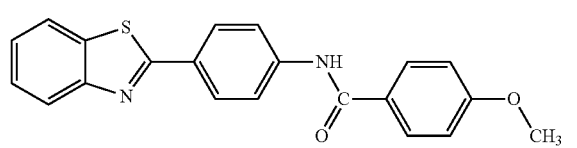

(56)
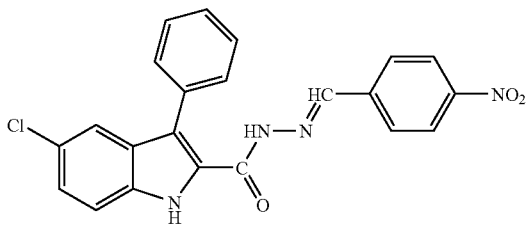

(57)
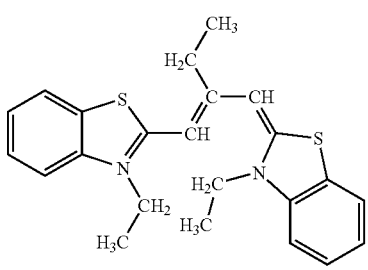

(58)
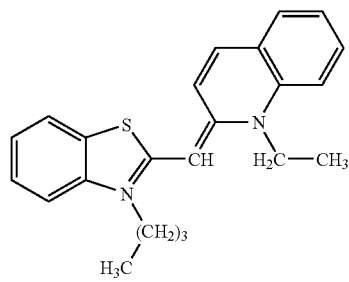

(59)
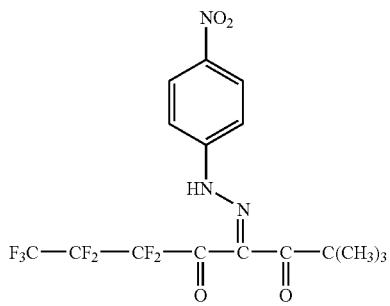

(60)
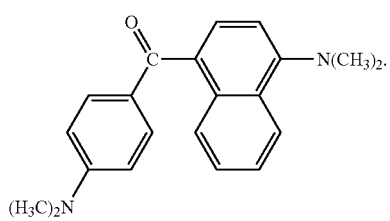

The compounds described above can be prepared according to methods known in the art.

In certain embodiments, the subject aromatic compounds can be chosen on the basis of their selectively for the ptc/smoothened pathway(s). This selectivity can be for the ptc/smoothened pathway(s) versus other steroid-mediated pathways (such as testosterone or estrogen mediated activities), as well as selectivity for particular ptc/smoothened pathways, e.g., which isotype specific for ptc (e.g., ptc-1, ptc-2). For instance, the subject method may employ aromatic compounds that do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc-related signaling.

In one embodiment, the subject aromatic compounds for use in the present methods have a $k_d$ for members of the nuclear hormone receptor superfamily of greater than 1 µM, and more specifically greater than 1 mM, e.g., it does not bind estrogen, testosterone receptors or the like. In one embodiment, the subject compounds have no estrogenic activity at physiological concentrations (e.g., in the range of 1 ng-1 mg/kg).

Thus, in one embodiment, untoward side effects that may be associated with certain members of the aromatic compounds can be reduced by, for example, using the drug screening assays described herein. The application of combinatorial and medicinal chemistry techniques to the aromatic compounds provides a means for reducing such unwanted negative side effects including personality changes, shortened life spans, cardiovascular diseases and vascular occlusion, organ toxicity, hyperglycemia and diabetes, Cushnoid features, "wasting" syndrome, steroidal glaucoma, hypertension, peptic ulcers, and increased susceptibility to infections. For certain embodiments, it will be beneficial to reduce the teratogenic activity relative to jervine, as for example, in the use of the subject method to selectively inhibit spermatogenesis.

Another aspect of the present invention relates to a method of modulating a differentiated state, survival, and/or proliferation of a cell having a ptc loss-of-function, hedgehog gain-of-function, or smoothened gain-of-function, by contacting the cells with an aromatic compound as set forth above according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The aromatic compound, whether inductive or anti-inductive with respect proliferation or differentiation of a given tissue, can be, as appropriate, any of the preparations described above.

For example, the present method of using subject aromatic compounds is applicable to cell culture techniques wherein, whether for genetic or biochemical reasons, the cells have a ptc loss-of-function, hedgehog gain-of-function, or smoothened gain-of-function phenotype. Alternatively, a subject aromatic compound may be employed in a related method directed towards cells which have a ptc loss-of-function, hedgehog gain-of-function, or smoothened gain-of-function phenotype. In vitro neuronal culture systems have proven to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with an aromatic compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motomeurons. Such neuronal cultures can be used as convenient assay systems as well as sources of implantable cells for therapeutic treatments.

In another embodiment, the subject method can be used in the treatment of neoplastic or hyperplastic transformations such as may occur in the central nervous system. For instance, the subject compounds can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas. In another embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the subject compounds can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, compounds of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of subject compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising subject compounds can be utilized in liver repair subsequent to a partial hepatectomy.

The generation of the pancreas and small intestine from the embryonic gut depends on intercellular signaling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al., *Curr. Biol.* 7:801-4 (1997). The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialized mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject compounds can be used to control or regulate the proliferation and/or differentiation of pancreatic tissue both in vivo and in vitro.

There are a wide variety of pathological cell proliferative and differentiative conditions for which the aromatic compounds of the present invention may provide therapeutic benefits, with the general strategy being, for example, the correction of abberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and/or smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and/or smoothened signaling may be indicated in disease progression, the subject aromatic compounds can be used to enhance regeneration of the tissue after anti-tumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and/or smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject compounds, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al., *Development* 124:53 (1997) report that Sonic hedgehog regulates lung mesenchymal cell proliferation in vivo. Accordingly, the present method can be used to regulate regeneration of lung tissue, e.g., in the treatment of emphysema.

Fujita et al., *Biochem. Biophys. Res. Commun.* 238:658 (1997) reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that ptc, hedgehog and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog, or their receptors in these tissues during development, be affected by treatment with the subject aromatic compounds. Such tumors include, but are by no means limited to, tumors related to Gorlin's syndrome (e.g., basal cell carcinoma, medulloblastoma, meningioma, etc.), tumors evidenced in pot knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising one or more of the subject compounds can be used in the in vitro generation of skeletal tissue, such as from skeletogenic stem cells, as well as the in vivo treatment of skeletal tissue deficiencies. The present invention particularly contemplates the use of subject compounds to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the methods of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a subject aromatic compound to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject regulators may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject methods in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al., *Clin. Orthop. Relat. Red* 252:129 (1990)), isolated chondrocytes (Grande et al., *J. Orthop. Res.* 7:208 (1989); and Takigawa et al., *Bone Miner* 2:449 (1987)), and chondrocytes attached to natural or synthetic polymers (Walitani et al., *J. Bone Jt. Surg.* 71B:74 (1989); Vacanti et al., *Plast. Reconstr. Surg.* 88:753 (1991); von Schroeder et al. *J. Biomed. Mater. Res.* 25:329 (1991); Freed et al., *J. Biomed. Mater. Res.* 27:11 (1993); and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a subject aromatic compound during certain stages of the culturing process in order to manage the rate of differentiation of chondrocytes and the formation of hypertrophic chrondrocytes in the culture.

In another embodiment, the implanted device is treated with a subject aromatic compound in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In other embodiments, the subject methods can be employed as part of a regimen for the generation of bone (osteogenesis) at a site in the animal where such skeletal tissue is deficient. Indian hedgehog (Ihh) is particularly associated with the hypertrophic chondrocytes that are ultimately replaced by osteoblasts. For instance, administration of a compound of the present invention can be employed as part of a method for regulating the rate of bone loss in a subject. For example, preparations comprising subject compounds can be employed to control endochondral ossification in the formation of a "model" for ossification.

In yet another embodiment of the present invention, a subject compound can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis (Bitgood et al., *Curr. Biol.* 6:298 (1996)). In an embodiment, the subject aromatic compound can be used as a contraceptive. In similar fashion, aromatic compounds of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a subject aromatic compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a subject compound can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of subject compounds can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a preparation of a subject compound into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject methods can also be used in the treatment of corneopathies marked by corneal epithelial cell proliferation, as for example in ocular epithelial disorders such as epithelial downgrowth or squamous cell carcinomas of the ocular surface.

Levine et al., *J. Neurosci.* 17:6277 (1997) show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al., *Development* 124:363 (1997) demonstrated that treatment of cultures of perinatal mouse retinal cells with the amino-terminal fragment of Sonic hedgehog results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject methods can be used in the treatment of proliferative diseases of retinal cells and regulate photoreceptor differentiation.

Yet another aspect of the present invention relates to the use of the subject methods to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject methods can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The subject method can also provide a process for extending the duration of depilation.

Moreover, because a subject compound will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, subject compounds can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concommitant relief of the inhibition of follicle cell proliferation.

The subject method can also be used in the treatment of folliculitis, such as folliculitis decalvans, folliculitis ulerythematosa reticulata or keloid folliculitis. For example, a cosmetic preparation of a subject compound can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a subject compound, e.g., which promotes quiescense or differentiation, can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a subject compound composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative subject compound, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange.

In still another embodiment, the subject method can be used in the treatment of human cancers, particularly basal cell carcinomas and other tumors of epithelial tissues such as the skin. For example, subject compounds can be employed, in the subject method, as part of a treatment for basal cell nevus syndrome (BCNS), and other human carcinomas, adenocarcinomas, sarcomas and the like.

In another embodiment, the subject method is used as part of a treatment of prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al., *Science* 277:1109-13 (1997); Xie et al., *Cancer Res.* 57:2369-72 (1997); Oro et al., *Science* 276:817-21 (1997); Xie et al., *Genes Chromosomes Cancer* 18:305-9 (1997); Stone et al., *Nature* 384:129-34 (1996); and Johnson et al., *Science* 272:1668-71 (1996).

The subject method can also be used to treatment patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject methods can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

It will be apparent to one of ordinary skill that certain instances described above may respond favorably to administration of a hedgehog agonist or antagonist, depending on the particular effect on the hedgehog pathway desired. For example, although a hedgehog agonist may be useful in maintaining a culture of undifferentiated stem cells, a hedgehog antagonist may be employed to maintain a differentiation state in a culture of differentiated cells. Such methods are considered to fall within the scope of the present invention.

In another aspect, the present invention provides pharmaceutical preparations comprising the subject aromatic compounds. The aromatic compounds for use in the subject method may be conveniently formulated for administration with a pharmaceutically acceptable and/or sterile medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the subject compounds, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the subject compounds suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Embodiments of the present invention also provide articles of manufacture that can include a packaging material and a pharmaceutical composition contained within the packaging material. The packaging material can comprise a label which indicates that the pharmaceutical composition can be used for treatment of one or more disorders identified above.

The pharmaceutical composition can include a compound according to the present invention. In addition to a compound of the present invention, the pharmaceutical may also contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

Thus, in one embodiment, the invention provides a pharmaceutical composition including a therapeutic agent and a compound of the invention. The compound is present in a concentration effective to treat cancer.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like.

Salts of the invention can include amine salts formed by the protonation of an amino group with inorganic acids such as hydrochloric acid, hydrobromic acid, hydroiodic acid, sulfuric acid, phosphoric acid, and the like. Salts of the invention can also include amine salts formed by the protonation of an amino group with suitable organic acids, such as p-toluenesulfonic acid, acetic acid, methanesulfonic acid and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

The pharmaceutical compositions for the administration of the compounds of this embodiment, either alone or in combination with other therapeutic agents, may conveniently be presented in dosage unit form and may be prepared by any of the methods well known in the art of pharmacy. All methods include bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal, urethral, or vaginal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one embodiment, the invention compounds are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment"

refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compounds of the present invention they may be used for example in amounts as noted in the Physician Desk Reference (PDR) or as otherwise determined by one having ordinary skill in the art.

In the treatment or prevention of conditions which involve cellular proliferation, an appropriate dosage level can generally be between about 0.01 and about 1000 mg per 1 kg of patient body weight per day which can be administered in single or multiple doses. For example, the dosage level can be between about 0.01 and about 250 mg/kg per day; more narrowly, between about 0.5 and about 100 mg/kg per day. A suitable dosage level can be between about 0.01 and about 250 mg/kg per day, between about 0.05 and about 100 mg/kg per day, or between about 0.1 and about 50 mg/kg per day, or about 1.0 mg/kg per day. For example, within this range the dosage can be between about 0.05 and about 0.5 mg/kg per day, or between about 0.5 and about 5 mg/kg per day, or between about 5 and about 50 mg/kg per day. For oral administration, the compositions can be provided in the form of tablets containing between about 1.0 and about 1,000 mg of the active ingredient, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, and about 1,000.0 mg of the active ingredient for the symptomatic adjustment of the dosage to the patient to be treated. The compounds can be administered on a regimen of 1 to 4 times per day, such as once or twice per day. There may be a period of no administration followed by another regimen of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the present invention can be used, alone or in combination with an effective amount of a therapeutic antibody (or therapeutic fragment thereof), a chemotherapeutic or an immunotoxic agent, for treatment of tumors. Illustrative examples of chemotherapeutic agents that can be used for this purpose include doxorubicin, docetaxel, or taxol. It should be further understood that the invention includes combination therapy including a compound of the invention, including but not limited to vasculostatic agents, such as tyrosine, serine or threonine kinase inhibitors, for example, Src-family inhibitors, and any chemotherapeutic agent or therapeutic antibody.

The subject aromatic compounds, and derivatives thereof, can be prepared readily by employing known synthetic methodology. As is well known in the art, these coupling reactions are carried out under relatively mild conditions and tolerate a wide range of "spectator" functionality. Additional compounds may be synthesized and tested in a combinatorial fashion, to facilitate the identification of additional compounds which may be employed in the subject method.

The aromatic compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog regulator lead compounds, as well as to refine the specificity, toxicity, and/or cytotoxic-kinetic profile of a lead compound. For instance, ptc, hedgehog, and smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened. Alternatively, bioactivity assays using cells with either a ptc gain-of-function, hedgehog loss-of-function, or smoothened loss-of-function, can be used to screen a library of the subject compounds for those having antagonist activity toward ptc or agonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

A variety of techniques are available in the art for generating combinatorial libraries of small organic molecules such as the subject aromatic compounds. See, for example, Blondelle et al., *Trends Anal. Chem.* 14:83 (1995); the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al., *JACS* 116:2661 (1994); Kerr et al., *JACS* 115:252 (1993); PCT publications WO92/10092, WO93/09668 and WO91/07087; and the Lerner et al. PCT publication WO93/20242). Accordingly, a variety of libraries on the order of about 100 to 1,000,000 or more diversomers of the subject compounds can be synthesized and screened for particular activity or property.

In an exemplary embodiment, a library of candidate compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with, for example, ptc loss-of-function, hedgehog gain-of-function, or smoothened gain-of-function cells for which a hedgehog agonist is sought. The diversomers can be released from the bead, e.g. by hydrolysis.

Many variations on the above and related pathways permit the synthesis of widely diverse libraries of compounds which may be tested as regulators of hedgehog function.

There are a variety of assays available for determining the ability of an aromatic compound such as a hedgehog antagonist to regulate ptc, smoothened, or hedgehog function, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are hedgehog antagonists.

In addition to cell-free assays, test compounds can also be tested in cell-based assays. In one embodiment, cells which have a ptc loss-of-function, hedgehog gain-of-function, or smoothened gain-of-function phenotype can be contacted with a test agent of interest, with the assay scoring for, e.g., inhibition of proliferation of the cell in the presence of the test agent.

In an exemplary embodiment, a library of candidate compounds obtained from ChemDiv, Inc. (San Diego, Calif.) was screened for Hh pathway modulators utilizing a scheme adapted to the techniques described in Chen et al., PNAS 99:14071-14076 (2002). Binding of the compounds to patched and smoothened was determined utilizing a scheme adapted to the techniques described in Chen et al., Genes & Dev. 16:2743-2748 (2002).

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are the patched gene (Hidalgo and Ingham, Development 110, 291-301 (1990); Marigo et al., 1996) and the vertebrate homologs of the drosophila cubitus interruptus gene, the GLI genes (Hui et al., Dev Biol 162:402-413 (1994)). Patched gene expression has been shown to be induced in cells of the limb bud and the neural plate that are responsive to Shh. (Marigo et al. PNAS 93:9346-51 (1996); Marigo et al. Development 122:1225-1233 (1996)). The Gli genes encode putative transcription factors having zinc finger DNA binding domains (Orenic et al. Genes & Dev 4:1053-1067 (1990); Kinzler et al. Mol Cell Biol 10:634-642 (1990)). Transcription of the Gli gene has been reported to be upregulated in response to hedgehog in limb buds, while transcription of the Gli3 gene is downregulated in response to hedgehog induction Narigo et al. Development 122:1225-1233 (1996)). By selecting transcriptional regulatory sequences from such target genes, e.g., from patched or Gli genes, that are responsible for the up- or down-regulation of these genes in response to hedgehog signaling, and operatively linking such promoters to a reporter gene, one can derive a transcription based assay which is sensitive to the ability of a specific test compound to modify hedgehog-mediated signaling pathways. Expression of the reporter gene, thus, provides a valuable screening tool for the development of compounds that act as antagonists to hedgehog.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc loss-of-function, hedgehog gain-of-function, smoothened gain-of-function, or stimulation by SHH themselves. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or antagonized the gain-of-function hedgehog or smoothened signal), e.g., the test compound is a potential hedgehog antagonist.

A particular advantage to the screening assays of the invention finds application to the design of personalized medicine. For example, a plurality of test agents can be arranged in an array, which can be an addressable array, on a solid support such as a microchip, on a glass slide, on a bead, or in a well, and the cells of a subject (e.g., a biopsy sample) can be contacted with the different test agents to identify one or more agents having desirable characteristics, including, for example, in addition to the ability to modulate ptc loss-of-function, hedgehog gain-of-function, smoothened gain-of-function, minimal or no toxicity to the cell, desirable solubility characteristics, and the like. Consequently, a treatment regimen may be tailored specifically to the individual based upon the subject's levels of ptc loss-of-function, hedgehog gain-of-function, smoothened gain-of-function.

Once disease is established and a treatment protocol is initiated, screening assays of the invention may be repeated on a regular basis to evaluate whether any of the levels of ptc loss-of-function, hedgehog gain-of-function, smoothened gain-of-function in the patient begins to approximate that which is observed in a normal patient. The results obtained from successive assays may be used to show the efficacy of treatment over a period ranging from several days to months. Accordingly, the invention is also directed to methods for monitoring a therapeutic regimen for treating a subject having cancer. A comparison of any of the levels of ptc loss-of-function, hedgehog gain-of-function, smoothened gain-of-function prior to and during therapy indicates the efficacy of the therapy. Therefore, one skilled in the art will be able to recognize and adjust the therapeutic approach as needed.

As used herein, a "corresponding normal sample" is any sample taken from a subject of similar species that is considered healthy or otherwise not suffering from a cancer disease being treated. As such, a normal/standard levels of ptc loss-of-function, hedgehog gain-of-function, smoothened gain-of-function denotes the level of ptc loss-of-function, hedgehog gain-of-function, smoothened gain-of-function present in a sample from the normal sample. A normal level of ptc loss-of-function, hedgehog gain-of-function, smoothened gain-of-function can be established by combining body fluids or cell extracts taken from normal healthy subjects, preferably human, with antibody to the proteins of interest under conditions suitable for ptc loss-of-function, hedgehog gain-of-function, smoothened gain-of-function. Levels of ptc loss-of-function, hedgehog gain-of-function, smoothened gain-of-function in subject, control, and disease samples from biopsied tissues can be compared with the standard values. Deviation between standard and subject values establishes the parameters for diagnosing and treating disease. A normal level of ptc loss-of-function, hedgehog gain-of-function, smoothened gain-of-function also can be determined as an average value taken from a population of subjects that is considered to be healthy, or is at least free of cancer. A variety of protocols including ELISA, RIA, and FACS are useful for measuring levels of ptc loss-of-function, hedgehog gain-of-function, smoothened gain-of-function, and provide a basis for diagnosing altered or abnormal levels ptc loss-of-function, hedgehog gain-of-function, smoothened gain-of-function.

Although the invention has been described with reference to the above examples, it will be understood that modifications and variations are encompassed within the spirit and scope of the invention. Accordingly, the invention is limited only by the following claims.

What is claimed is:

1. A compound having structure (I):

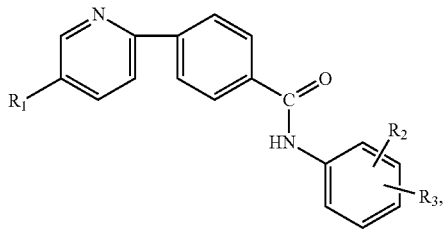

or a pharmaceutically acceptable salt thereof, wherein:
$R_1$ is selected from a group consisting of ethyl, n-propyl and n-amyl;
$R_2$ is selected from a group consisting of hydrogen, chlorine, methyl, and methoxy;
$R_3$ is selected from a group consisting of methyl, chlorine, iodine, trifluoromethyl, and methoxy; and
wherein the compound inhibits a hedgehog signaling pathway.

2. The compound of claim 1, wherein the compound having structure (I) is selected from the group of compounds having the formulae (1)-(7):

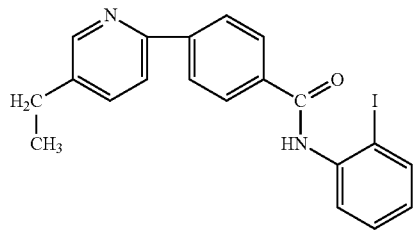

(1)

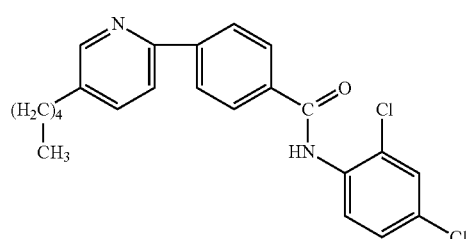

(2)

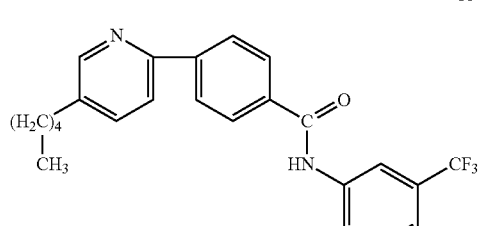

(3)

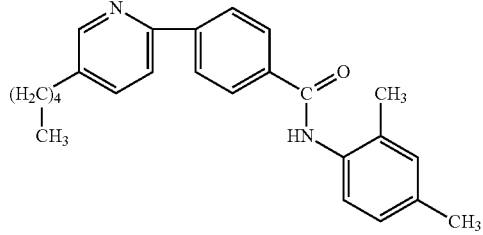

(4)

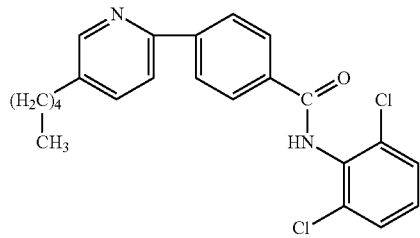

(5)

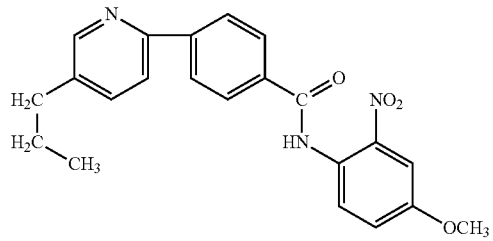

(6)

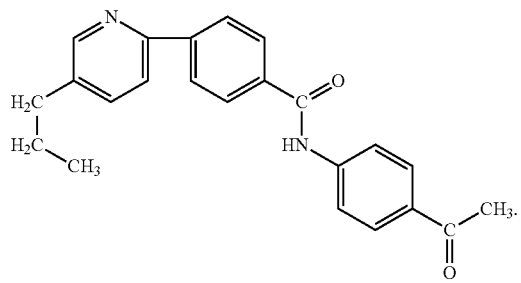

(7)

3. A compound having structure (II):

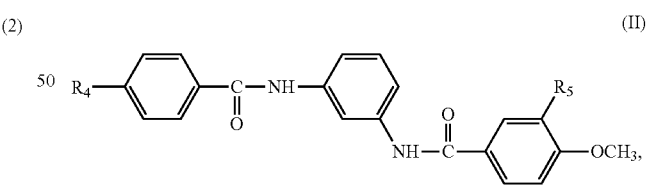

(II)

or a pharmaceutically acceptable salt thereof, wherein:
$R_4$ is selected from a group consisting of tert-butyl and chlorine; and
$R_5$ is selected from a group consisting of nitro and bromine; and
wherein the compound inhibits a hedgehog signaling pathway.

4. The compound of claim 3, wherein the compound having structure (II) is selected from a group consisting of compounds having formulae (8) and (9):

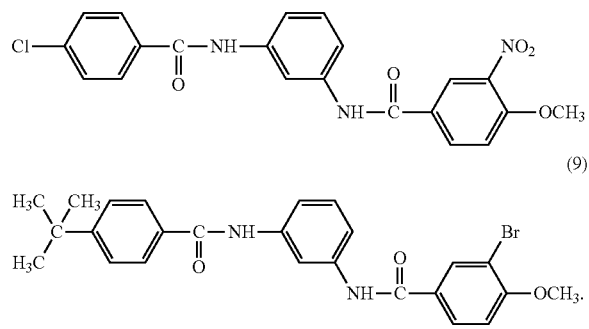

5. A pharmaceutical composition comprising the compound of claim 1 or claim 3, in a pharmaceutically acceptable carrier.

6. An article of manufacture comprising packaging material and a pharmaceutical composition contained within the packaging material, wherein the packaging material comprises a label which indicates that the pharmaceutical composition can be used for treatment of disorders and wherein said pharmaceutical composition comprises the compound of claim 1 or claim 3.

* * * * *